United States Patent [19]

Nagai

[11] Patent Number: 4,904,534
[45] Date of Patent: Feb. 27, 1990

[54] IMPLANT MATERIAL

[75] Inventor: Hirosi Nagai, Chofu, Japan

[73] Assignee: Kureha Kagaku Kogyo Kabushiki Kaisha, Japan

[21] Appl. No.: 370,119

[22] Filed: Jun. 23, 1989

Related U.S. Application Data

[63] Continuation of Ser. No. 120,708, Nov. 16, 1987, abandoned, which is a continuation of Ser. No. 870,990, Jun. 5, 1986, abandoned.

[30] Foreign Application Priority Data

Jun. 10, 1985 [JP] Japan .................................. 60-125696
Sep. 20, 1985 [JP] Japan .................................. 60-207836

[51] Int. Cl.$^4$ ................................................ A61F 1/00
[52] U.S. Cl. .................................. 428/457; 433/201.1; 433/222.1
[58] Field of Search ........................ 433/201.1, 222.1; 523/212, 116, 118; 428/457

[56] References Cited

U.S. PATENT DOCUMENTS

| | | | |
|---|---|---|---|
| 3,609,867 | 10/1971 | Hodosh | 433/201.1 |
| 3,863,344 | 2/1975 | Pillet | 433/201.1 |
| 4,159,358 | 6/1979 | Hench et al. | 623/16 X |
| 4,178,686 | 12/1979 | Riess et al. | 433/201.1 |
| 4,302,381 | 11/1981 | Omura et al. | 523/118 X |
| 4,347,174 | 8/1982 | Nagase et al. | 523/212 X |
| 4,386,912 | 6/1983 | Nagase et al. | 523/116 X |
| 4,437,191 | 3/1984 | Van der Zel et al. | 623/16 |
| 4,599,085 | 7/1986 | Riess et al. | 623/16 |
| 4,610,693 | 9/1986 | Niwa et al. | 623/16 |
| 4,617,327 | 10/1986 | Podszun | 523/116 |
| 4,705,836 | 11/1987 | Ohtsuka et al. | 523/118 X |

Primary Examiner—Nancy A. B. Swisher
Attorney, Agent, or Firm—Nixon & Vanderhye

[57] ABSTRACT

Disclosed herein is a novel implant material excellent in biocompatibility, stability in living body and mechanical properties, comprising a metallic material and a layer of a thermosetting resin or a layer of a composition comprising the thermosetting resin and hydroxyapatite, the layer of the thermosetting resin or the layer of the composition being formed around the metallic material.

13 Claims, 2 Drawing Sheets

IMPLANT MATERIAL

This is a continuation of application Ser. No. 120,708, filed Nov. 16, 1987, now abandoned, which is a continuation of application Ser. No. 870,990, filed June 5, 1986, now abandoned.

BACKGROUND OF THE INVENTION

The present invention relates to a novel implant material excellent in biocompatibility, stability in living body and mechanical properties, comprising a metallic material and a layer of a thermosetting resin or a layer of a composition comprising the thermosetting resin and hydroxyapatite, the layer of the thermosetting resin or the layer of the composition being formed around the metallic material.

In recent years, with the development of biotechnology, implant techniques which implant artificial material processed in a shape of joint or radix dentis into bone tissue of human body have been highlighted.

As the artificial material used in the implant technique, metallic materials such as alloys of cobalt and chromium, titanium, tantalum and the like, and ceramic materials such as hydroxyapatite, zirconia, alumina, glassy carbon and the like have hitherto been known. However although the metallic materials are excellent in mechanical strength, they are poor in biocompatibility and some of them are injurious due to the eduction of metal ions. On the other hand, the ceramic materials are excellent in biocompatibility, however, they are still poor in mechanical properties.

Namely, the conventional artificial materials have one or more of demerits concerning toxicity, compatibility bones, mechanical properties or durability and accordingly, they can not be said to be the satisfactory implant materials. Accordingly, trials of combining different materials have been carried out in order to settle the above-mentioned problems.

For instance, Japanese Patent Application Laying-Open (KOKAI) No. 53-28997 (1978) discloses, as an implant material in which a metallic material and another material have been integrated into one body, the implant material made by forming a melt-ejected layer of powdery ceramic or powdery hydroxyapatite on the surface of a metallic material. Such an implant material is expected from the view point of making the most of both the biocompatibility of hydroxyapatite and the mechanical strength of metallic material, however, cracks are apt to be formed in the melt-ejected layer due to the difference of thermal expansion between the metallic material and the melt-ejected material layer, and eduction of metal ions from the thus formed crack is feared.

In addition, Japanese Patent Application Laying-Open (KOKAI) No. 57-156757 (1982) discloses an implant material made by coating the outer surface of a metallic material with a composition singly formed by a thermoplastic polymer such as polysulfon, high density polyethylene, poly(methyl methacrylate) and the like, or formed by adding from 20 to 30% by weight of an inorganic material such as calcium phosphate, hydroxyapatite and the like to the thermoplastic polymer.

However, the thermoplastic polymers are insufficient in the adhesion to the metallic material, the stability in living body, the osteogenesity and the mechanical properties and accordingly, they are not practically reliable.

As a result of the present inventor's studies for developing an implant material which is excellent in the adhesion to the metallic material, the osteogenesity, the mechanical properties and the feeling on actual use thereof and is reliable on practical use, he has found that the implant material obtained by forming a layer of thermosetting resin which is favorable in biocompatibility and stability in living body, around the outer surface of the metallic material solves the demerits of the conventional implant materials and based on the finding, the present invention has been attained.

SUMMARY OF THE INVENTION

In an aspect of the present invention, provided there is an implant material which is excellent in the adhesion to a metallic material, mechanical properties, the stability in living body and osteogenesity, the implant material being produced by forming a layer of a thermosetting resin, which is excellent in the stability in a living body and the biocompatibility, around the metallic material or a layer of a composition comprising the thermosetting resin and hydroxyapatite around the outer surface of the metallic material.

BRIEF EXPLATATION OF DRAWINGS

Of the attached drawings, FIGS. 1 and 3 and FIGS. 2 and 4 are respectively the vertical sectional view and the cross sectional view of one of the implant materials according to the present invention. FIG. 5 is a graph showing a relationship between temperature and time as explained in Example 2.

DETAILED DESCRIPTION OF THE INVENTION

Figure 1:
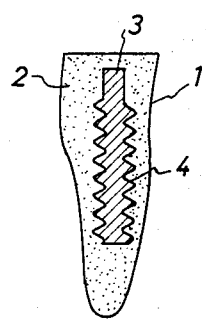
Figure 2:
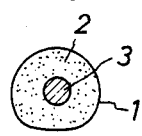

Although the thermosetting resin according to the present invention is excellent in the adhesion to the metallic material, since it is implanted in a living body for a long period of time, it is necessary that the thermosetting resin is excellent in biocompatibility, does not self-deteriorate and does not cause the collapse of the living cells. For instance, as such a thermosetting resin, a polymer which is prepared by an addition polymerization of a monomer such as bisphenol A diglycidyl methacrylate; 1,3-butanediol dimethacrylate, ethylene glycol dimethacrylate (hereinafter referred to as 1G), diethylene glycol dimethacrylate (hereinafter referred to as 2G) and triethylene glycol dimethacrylate (hereinafter referred to as 3G) may be exemplified, and in particular, 3G is harmless to a living body, has a merit of easily forming bones and accordingly, is favorable. The above-mentioned thermosetting resin is singly used or used as a mixture.

In addition, in the case where the composition comprising the thermosetting resin and hydroxyapatite is used, since the thermosetting resin is excellent in retaining hydroxyapatite and in biocompatibility and hydroxyapatite is especially excellent in biocompatibility, in particular, in osteogenesity, the presence of hydroxyapatite in the composition gives the implant material superior biocompatibility.

On the other hand, the layer made only of the thermosetting resin is excellent in hardness and the adhesion to the metallic material.

Accordingly, whether the layer of the present material made only of the thermosetting resin or the layer of the present material made of the composition of the resin and hydroxyapatite is used, should be decided in consideration of the place of use, the use conditions and the shape in use of the present material.

Hydroxyapatite used according to the present invention is synthetic- or natural hydroxyapatite, a calcined product thereof or a mixture thereof.

As synthetic hydroxyapatite, those available by known processes of production, for instance, a dry process disclosed in "CERAMICS", Vol. 10(7), page 461 (1975) wherein $Ca_3(PO_4)_2$ and an excess of $CaCO_3$ are reacted in a water vapour flow at 900° to 1300° C., a wet process disclosed in Japanese Patent Application Laying-Open (KOKAI) No. 56-45814 (1981) wherein microparticles of calcium hydroxide are reacted with an aqueous solution of phosphoric acid under high speed stirring and a wet process disclosed in "Angewandte Chem., 67, page 327 (1955) wherein an aqueous solution of $Ca(NO_3)_2$ and an aqueous solution of $(NH_4)_2HPO_4$ are reacted under $NH_4OH$-alkaline conditions, and the calcined product thereof may be exemplified.

Natural hydroxyapatite can be produced by using natural bones as a starting material, for instance, by calcining the backbone of a cow or ox at a temperature around 800° C. and removing the organic materials. Hydroxyapatite may be that, if necessary, which contains whitlockite or a foreign element such as fluorine, iron, etc.

The grain size of hydroxyapatite is less than 1000 micrometers in diameter, preferably in the range of from 0.01 to 100 micrometers from the view points of the processability, the handling and the mechanical strength.

The metallic material according to the present invention includes all the known metals and alloys, however, those of alloys of Co-Cr-Ni series and Co-Cr-Mo series, stainless steels 18-8, 316L, titanium and tantalum which scarcely harm the tissue of living body, have sufficient mechanical strength and is dense or porous material having been used as the material for producing artificial bones are preferable.

In order to devise the anchor effect with the resin composition and to disperse the external stress after implanting, independent and/or continuous ditches or grooves may be installed on the outer surface of the metallic material.

The shape and the size of the metallic material are not specifically limited, and the shape can be pin-type, screw-type, blade-type, anchor-type, plate-type, mesh-type, etc. The cross-section of the metallic material may be any one of square, circle, oval, etc.

As the method for obtaining the implant material according to the present invention, there is no particularly limited method, and for instance, the implant material can be produced by (1) setting a core metallic material obtained by molding, sintering, casting, cutting or grinding and further subjecting to surface treatment in a mold, (2) pouring a monomer of the thermosetting resin to which a hardening agent, etc. has been admixed preliminarily into the mold, (3) heating the core metallic material and the monomer in the mold and after hardening the monomer, and (4) cutting and grinding the outer surface of the thus hardened resin composition according to the necessity.

In addition, following the conventional thermosetting method, internal strains are caused in the resin layer, thereby easily making cracks on the interface to the core material. Accordingly, it is necessary to carefully select the condition of hardening such as temperature, time, etc.

The above-mentioned problem in the conventional thermosetting method can be settled by adding powdery or granular thermosetting polymer to the monomer of the thermosetting resin. The weight ratio of the polymer to the monomer is 5/95 to 95/5, preferably 20/80 to 80/20. The shape of the thus added polymer is not particularly limited, and the particle diameter of the polymer is ordinarily 2 to 500 μm, preferably 10 to 200 μm. As the polymer, a polymer which is prepared by addition polymerization of a monomer such as bisphenol A diglycidyl methacrylate; 1,3-butanediol dimethacrylate, 1G, 2G and 3G may be mentioned. In particular, 3G is harmless to a living body, has the advantage of easily forming bones and accordingly, is preferred. The above mentioned thermosetting resin is used by itself or used as a mixture.

The outer surface of the resin composition may be smooth or uneven such as screw-like.

The suitable place in a human body for applying the implant material according to the present invention is not specifically provided, however, it will not be necessary to say that the implant material may be applied within tooth and bone, under the periosteum and with the mucous membrane.

In addition, in the case of using the implant material according to the present invention as the artificial dental tooth root, it is one of the characteristics of the implant material that the material does not give the abnormal feeling because of the appropriate elastic modulus and hardness thereof.

Besides, on the outside of the resin composition which positioned near the epiterium of the inner border, a structured body made only of hydroxyapatite may be installed, and in addition, the resin composition may be formed in the shape of a sword, thereby increasing the adhesion to the epiterium.

The implant material according to the present invention will be briefly explained while referring to Figures as follows.

Figure 3:
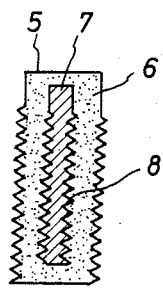
Figure 4:
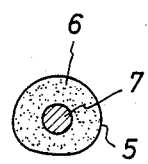
Figure 5:
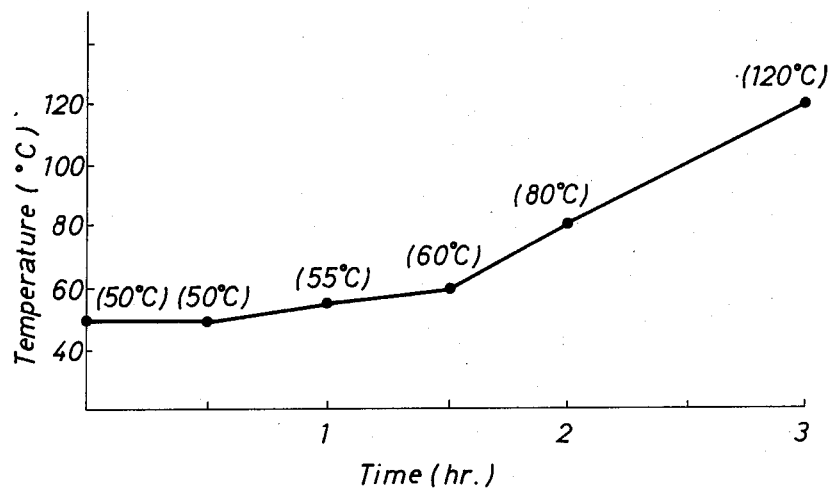

In the vertical section shown in FIGS. 1 and 3, the main body of the implant material according to the present invention (1 and 5) has a structure that the metallic core (3 and 7) is coated by the resin composition (2 and 6).

Namely, for instance, the metallic core (3 and 7) of the main body of the implant material (1 and 5) is formed by an alloy of titanium or cobalt series, and the outer surface of the core (3 and 7) is coated by a layer of a polymer of triethylene glycol dimethacrylate or a layer of a resin composition (2 and 6) made by adding 70% by weight of hydroxyapatite to 30% by weight of a polymer of triethylene glycol dimethacrylate, a screw-type groove (4 and 8) having been provided on the core (3 and 7).

To the upper part of the implant material according to the present invention, a ready-made artificial dental crown of standard type, which has been freely selected, may be adhered and fixed, and the thus treated material may be used.

The present invention will be concretely explained while referring to Examples as follows.

EXAMPLE 1:

Into a separable flask, 50 g of 3G monomer (made by MITSUBISHI Rayon Co., Ltd. under the name of ACRYLESTER 3ED) and 50 g of 3G polymer of 23 μm in mean particle diameter were introduced, and the content of the flask was stirred at room temperature under vacuum to carry out deaeration thereof.

Then, 0.5% by weight of a hardening agent (t-butyl peroctoate) was added into the flask, and the content of the flask was stirred for 30 minutes.

The thus prepared liquid resin was poured into a glass tube of 4 mm in internal diameter in which a pure titanium stick of 3 mm in diameter and 100 mm in length had been fixed, and the liquid resin was subjected to hardening treatment to obtain an implant material under the following conditions:

The liquid resin was heated for 5 hours at 55° C., 2 hours at 65° C., 1 hour at 70° C., 1 hour at 100° C., 30 min. at 110° C. and then 30 min. at 120° C.

EXAMPLE 2:

Into a separable flask, 25 g of 3G monomer (same as in Example 1), 5 g of 3G polymer (same as in Example 1) and 70 g of hydroxyapatite of 4 μm in average particle diameter were introduced, and the content of the flask was stirred at room temperature under vacuum to carry out deaeration thereof.

Then, 0.3% by weight of the same hardening agent as in Example 1 (to 3G monomer) was added to the content of the flask, and the content of the flask was stirred for 30 minutes.

The thus prepared composition was poured into a glass tube of 5 mm in inner diameter in which a pure titanium stick of 3 mm in diameter and 50 mm in length had been fixed. Then, the glass tube was placed in an autoclave for dental use (manufactured by Shofu Dental Mfg. Co., Ltd.) filled with nitrogen gas of a starting pressure of 3 kg/cm² and the composition in the tube was subjected to hardening treatment by heating

EXAMPLE 3:

Each of the implant materials respectively prepared in Examples 1 and 2 were processed into the shape of 5 mm in diameter and 15 mm in length, and after grinding and smoothing the surface thereof, the thus processed implant materials were put into the alveolar bone of an adult dog.

As a result of observation of the thus treated implanted materials by X-rays, a favorable bone-formations were confirmed without any abnormal findings, such as inflammation, after 12 months of applications.

What is claimed is:

1. An implant material comprising a metallic material and a layer of a thermosetting resin thereon or a layer of a composition comprising a mixture of a thermosetting resin with hydroxyapatite particles therein, the thermosetting resin having excellent stability in a living body and being bicompatible, the layer of the thermosetting resin or the layer of the composition being formed around and adhered to the metallic material.

2. An implant material according to claim 1, wherein the weight ratio of said thermosetting resin to hydroxyapatite is in the range of from 65/35 to 15/85.

3. An implant material according to claim 1, wherein said thermosetting resin is a polymer of a monomer selected from the group consisting of bisphenol A diglycidyl methacrylate, 1,3-butanediol dimethacrylate, ethylene glycol dimethacrylate, diethylene glycol dimethacrylate and triethylene glycol dimethacrylate and a mixture thereof.

4. An implant material according to claim 3, wherein said thermosetting resin is a polymer of triethylene glycol dimethacrylate.

5. An implant material according to claim 1, wherein the mean diameter of said hydroxyapatite particles is less than 1000 μm.

6. An implant material according to claim 1, wherein said thermosetting resin is prepared by mixing from 5–95 wt. % particles of the polymer into the corresponding monomer prior to hardening the resin.

7. An implant material according to claim 6, wherein the diameter of said polymer particles mixed into the monomer is 2–500 μm.

8. A biocompatible implant comprising a metallic core material having attached thereto as an outer coating a layer of a thermosetting resin composition, optionally with hydroxyapatite particles distributed therein, the thermosetting resin being stable in a living body and biocompatible with adjacent body tissue.

9. The biocompatible implant of claim 8, wherein the thermosetting resin composition, prior to thermoset, contained particles of the thermosetting resin distributed throughout the corresponding monomer.

10. The biocompatible implant of claim 9, wherein the interface between the metallic core and the thermosetting resin composition is uniform and devoid of cracks.

11. The implant of claim 8, wherein the metallic core has a plurality of grooved anchoring means on its outer surface for dispersing external stress after implantation.

12. A biocompatible artificial tooth of a metallic core and an outer coating of thermosetting resin composition having an elastic modulus and hardness similar to a natural bone, the thermosetting resin composition containing a polymer of triethylene glycol dimethacrylate.

13. An biocompatible implantable artificial tooth of a metallic core and an outer coating of a thermosetting resin composition having an elastic modulus and hardness similar to a natural bone, the thermosetting resin composition containing a polymer of triethylene glycol dimethacrylate with particles of hydroxyapatite distributed therein, the weight ratio of thermosetting resin to hydroxyapatite in the range of 65:35 to 15:85.

* * * * *